United States Patent [19]

Harrison

[11] 4,402,309
[45] Sep. 6, 1983

[54] THERAPEUTIC MAGNETIC ELECTRODE
[75] Inventor: William H. Harrison, Woodland Hills, Calif.
[73] Assignee: Donald L. Morton & Associates, Pacific Palisades, Calif.
[21] Appl. No.: 313,656
[22] Filed: Oct. 22, 1981
[51] Int. Cl.³ .............................................. A61N 1/42
[52] U.S. Cl. .................................... 128/1.3; 128/804; 219/10.79
[58] Field of Search ......................... 128/1.3, 1.5, 804; 219/10.79

[56] References Cited
U.S. PATENT DOCUMENTS

| 2,478,640 | 8/1949 | Roberds | 219/10.79 X |
| 2,515,874 | 7/1950 | Hoyler et al. | 219/10.79 X |
| 2,641,682 | 6/1953 | McKenna | 219/10.79 |
| 2,756,313 | 7/1956 | Ceter | 219/10.79 X |
| 2,790,055 | 4/1957 | Van Iperen | 219/10.79 |
| 4,186,729 | 2/1980 | Harrison | 128/804 |

Primary Examiner—Lee S. Cohen
Attorney, Agent, or Firm—Poms, Smith, Lande & Rose

[57] ABSTRACT

An electrode of the self-resonant, single-turn loop type adapted for attachment to a source of radio frequency energy to produce deep-heating by hyperthermia. The electrode is characterized by being a long cylindrical electrode having a small diameter to length radio as, for example, 0.5 to 1. The electrode is in the form of a cylinder having a gap along one side to which a plurality of capacitor plates are electrically connected radially outward and in parallel spaced relationship with a dielectric material disposed therebetween.

13 Claims, 9 Drawing Figures

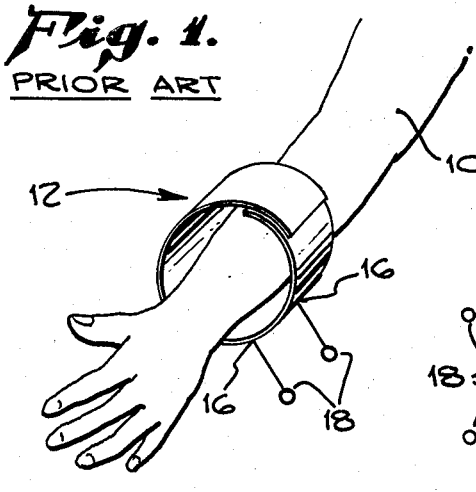
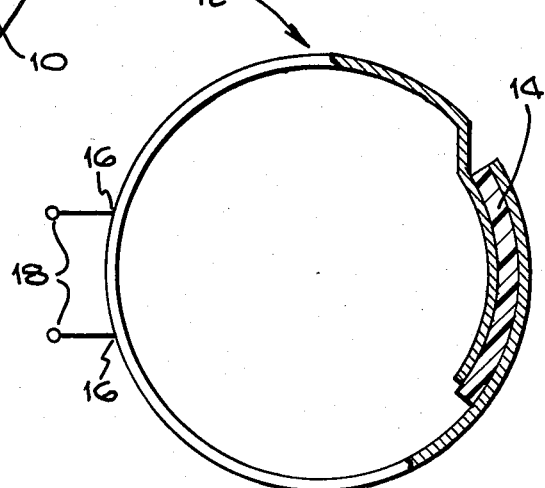
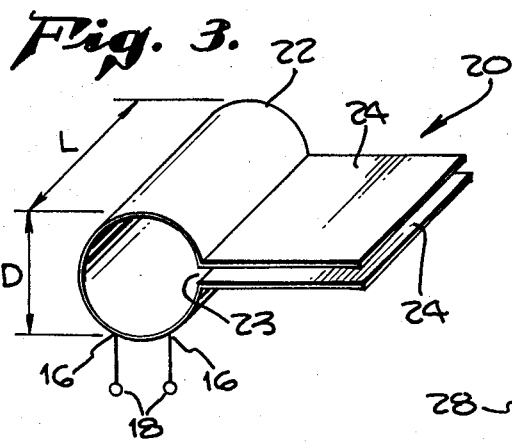
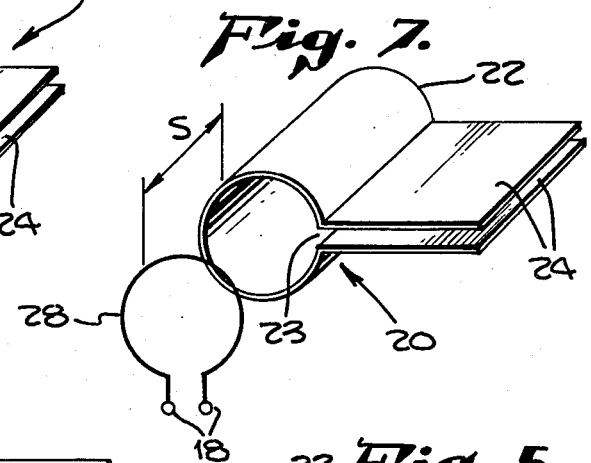
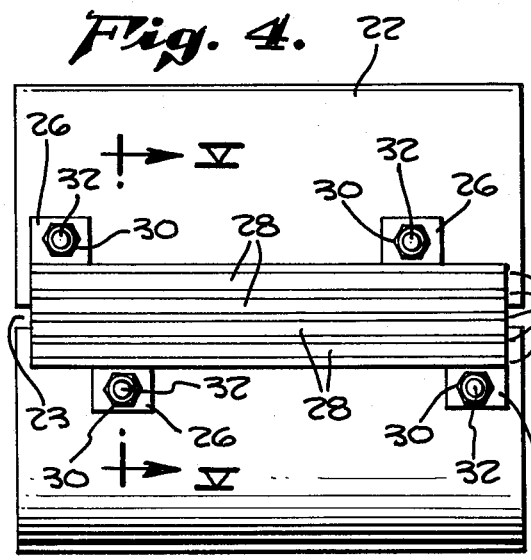
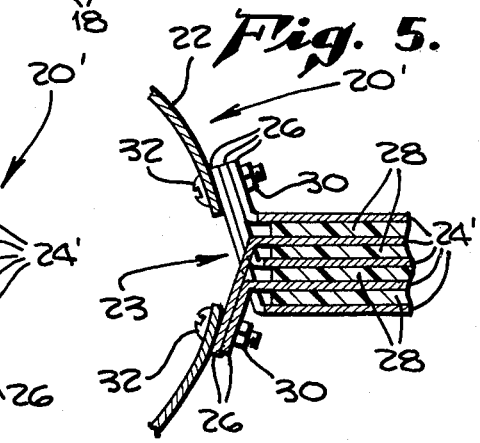

THERAPEUTIC MAGNETIC ELECTRODE

BACKGROUND OF THE INVENTION

The present invention relates to electrodes used in medical treatment and, more particularly, to electrodes employed with radio frequency energy to produce deep heating by hyperthermia.

The therapeutic effects of heat have been known for a long time. Of particular interest, it is has been found that tumors can be heated and, thereby, destroyed by the heat alone or with the heat adding to the effects of other treatment such as chemotherapy. Likewise, it has been known that radio frequency energy can be employed to cause by traditional diathermy apparatus.

Recently, in my U.S. Pat. No. 4,186,729, an electrode was shown which allows radio frequency energy to be employed to cause deep-heating within an animal body. A simplified drawing of an electrode as disclosed therein is shown in FIG. 1. Prior to my Deep-Heating Electrode, a person 10 having a tumor situated deep within his body was virtually unable to have sufficient energy transferred thereto to cause therapuetic heating of the tumor. Before my invention, such heating could only occur effectively by surgically exposing the tumor and placing traditional diathermy electrodes in electrical contact with opposing surfaces of the tissue to cause the energy to pass therethrough. Attempts to use such traditional diathermy apparatus by placing the electrodes in contact with the exterior surfaces of the body merely cause the energy to be dissipated in the skin and subcutaneous fat layers with very little, if any, heating occuring in the deep areas where desired.

According to my invention as disclosed in the above-referenced patent, an electrode 12 in the form of a cylinder, as shown, can be placed about the body of the person 10 over the area of the tumor and deep-heating energy transmitted thereto if the electrode 12 is in the form of a single-turn self-resonant loop which causes a series of concentric force lines of substantially equal energy to be created inside the cylinder.

The construction of such an electrode is typified by the example of FIG. 2 (which appeared as FIG. 2 in the above-referenced patent). In that embodiment, electrode 12 comprises a strip of conductive material formed into a cylinder having the ends thereof in overlapping, non-contacting relationship. While an air dielectric could be employed, it is preferred that a material such as Teflon be disposed between the overlapping ends of electrode 12 such as that labeled 14 in FIG. 2. The area of overlap and the dielectric material are chosen such that when electrode 12 is excited by connecting it a source of radio frequency energy as by providing taps 16 to which a connector 18 providing the RF energy can be connected, maximum energy is transferred.

Typically, the electrodes designed using the above techniques have had an aspect ratio of approximately 2 to 1. That is, the diameter is twice the cylinder length. This has resulted in a very efficient electrode and, in general, heated the desired volume within the cylinder. An additional need, however, has been established for a long cylindrical electrode where the aspect ratio is approximately 0.5 to 1. That is, the diameter being one-half the cylinder length. This added length configuration is desired to heat a greater portion of a limb (i.e., arm, leg) or possibly a larger section of the body, in a uniform manner, thus pre-heating the blood entering the lesion area. It has also been found to have therapeutic benefit for the typical diathermy type treatments such as muscle and joint pain.

In attempting to construct such an electrode of useable dimensions applying the above-described technique of end overlap, considerable problems were encountered. For example, in a cylinder of 13 centimeters diameter and 23 centimeters length, the inductance is very low and, therefore, a large amount of capacity is required to resonate the cylinder. To accomplish resonance with a convenient overlap required a dielectric thickness of 0.007 inches, thus critically limiting the electrode's power handling capability.

Early experiments with such electrodes and variations thereof also indicated a potential problem of non-uniform and un-controlled heat generation distribution throughout the length thereof.

Wherefore, it is the object of the present invention to provide an electrode for use in medical treatment by hyperthermia using the magnetic field approach wherein the electrode has a long length as compared to the diameter and in which the electrode's design can control the distribution of energy over the electrode cylinder length including the production of uniform heating throughout.

SUMMARY

The foregoing objectives have been met in an electrode for use in the treatment of animal tissue by hyperthermia comprising electrically conductive material disposed to form a resonance slotted cylinder which is adapted for coupling to a supply of radio frequency energy and wherein the slotted cylinder has a pair of capacitor plates attached radially to respective sides of the slot in parallel spaced relationship with a dielectric material disposed therebetween.

In the preferred embodiment, a plurality of capacitor plate pairs are attached to the cylinder at specific locations along the slot length to control the thermal pattern for a specific application such as producing uniform heating over an extended length.

DESCRIPTION OF THE DRAWINGS

FIG. 1 is a simplified drawing of a prior art cylindrical electrode disposed for treatment of a human limb.

FIG. 2 is a simplified drawing showing the typical construction of prior art cylindrical electrodes such as the one of FIG. 1.

FIG. 3 is a simplified drawing of the present invention in its basic form showing the elongated cylinder and the parallel plate capacitor attachment thereto.

FIG. 4 illustrates the preferred multiple capacitor plate construction of the present invention and one method of attachment to the slotted cylinder.

FIG. 5 presents a cross-section view of FIG. 4 giving more detail of a convenient method of capacitor connection to the slotted cylinder.

FIG. 7 shows an inductive loop method of connecting RF energy into the electrode of the present invention.

DESCRIPTION OF THE BASIC AND PREFERRED EMBODIMENTS

Figure 6:
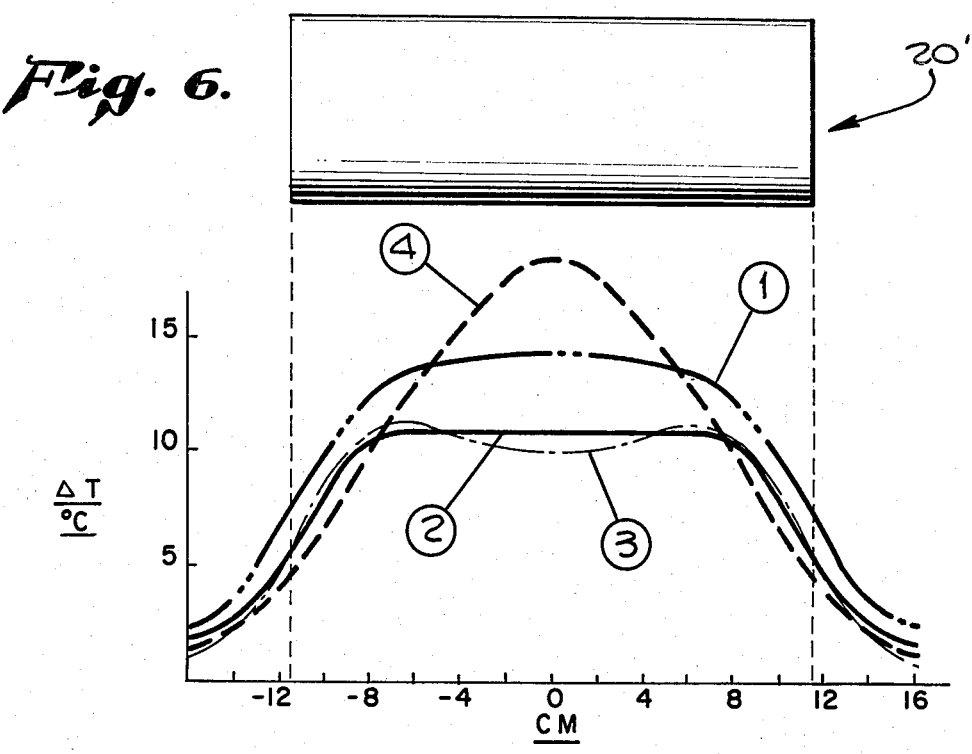
FIG. 6 is a series of thermal response curves with the capacitor plates attached at specific locations along the cylindrical length.

FIG. 3 illustrates the general configuration of an electrode 20 according to the present invention in its basic form. Electrode 20 comprises a slotted cylinder 22 having a diameter D and a length L where the dimensions are chosen to contain a specific section of the body for heating. Capacitor plates 24 are electrically connected along one edge to respective sides of the slot 23 in cylinder 22 and extend radially outward in parallel, close adjacent, spaced relationship. The capacitor plates 24 are used to resonate the slotted cylinder 22 and, therefore, must be sized accordingly. A single pair of plates 24 can be used, but, as will be seen, in such a configuration the plate dimensions can become inconveniently large. For such cases, an alternate and preferred embodiment is described hereinafter.

As a practical demonstration, an elongated cylinder having a diameter D=13 cm and a length L=23 cm has a measured inductance of approximately 60 nanohenries and requires a resonating capacitance of 2300 pf. for operation at the usual 13.56 MHz medical frequency. Thus, with a plate separation of, for example 0.79 mm and using Teflon insulation, a surface area of 1000 sq. cm, i.e. an inconvenient 23 cm wide by 43.5 cm long is required. Because of this problem, the preferred embodiment of FIG. 4 was devised.

In the preferred electrode 20' of FIG. 4 (shown in great detail in partial cutaway side view in FIG. 5), the capacitor plates 24' are provided with tabs 26 of progressively increasing length. The tabs 26 for alternate plates 24' are also offset from one another and faced in opposite directions whereby the stacked arrangement shown in FIG. 4 and FIG. 5 can be achieved. It is preferred that Teflon dielectric 28 be placed between the plates 24'. It is convenient to drill an aligned bore 30 through the tabs 26 and sidewalls of slotted cylinder 22 adjacent slot 23 and attach the tabs 26 to slotted cylinder 22 with bolts 32. Other convenient forms of fastening such as blind rivets could also be used.

In relation to the above-described preferred embodiment of FIGS. 4 and 5, in a tested example five plates were used to obtain the required surface area while maintaining a plate separation of 0.79 mm, thus reducing the length to 11 cm from the original 43.5 cm.

Having solved the sizing problem by the preferred embodiment of FIGS. 4 and 5, temperature distribution measurements were then made using an elongated cylinder electrode 20' to heat a phantom made of a thin plastic cylinder filled with a gelatin-like material simulating the conductivity and dielectric constant of human muscle tissue. Temperature measurements were made progressively along the phantom's length with a needle thermister temperature probe. The heating patterns are measured are shown in FIG. 6.

Curve #1 shows the relative temperature increase measured along the length of the phantom load which was placed inside the electrode 20'. In that particular case, the capacitor plates 24' were attached continuously to the cylinder electrode 20' along the gap 23 in the manner of the electrode of FIG. 3. As can be seen, the heating pattern produced is not uniform across the electrode length, thus suggesting a concentration of current near the center of the cylindrical length similar to that obtained with a shorter cylinder length.

Various attachments of the capacitor plates 24' were then tested which demonstrated that the current flow can be controlled to produce desired characteristics including uniform heating over a major portion of the electrode cylinder length as depicted in curve #2. It was found that by attaching the plates 24' only at the extreme ends, a slight nulling effect was achieved as shown in curve #3. To further demonstrate the heating pattern control which can be obtained, when the capacitor plates 24' were centrally attached, curve #4 was obtained.

Figure 8:
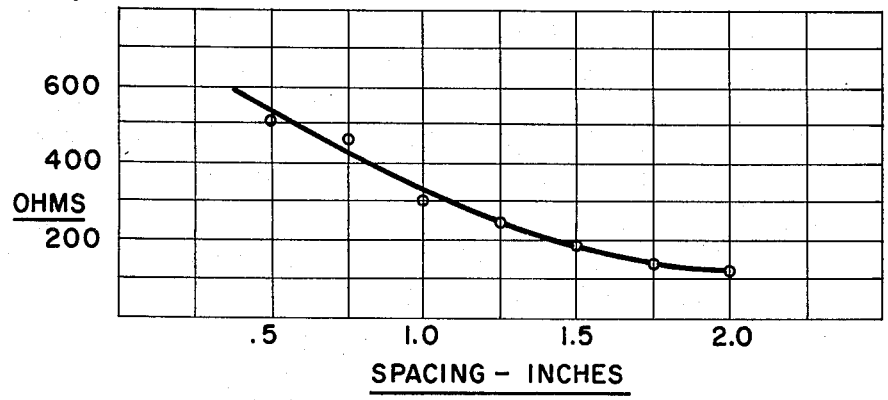
FIG. 8 is a graph showing the measured impedance at the connecting loop terminals of FIG. 7 for various spacings "S" in FIG. 8.

Radio frequency (RF) energy can be coupled to the electrode of the present invention by any conventional matching network means. For example, in FIG. 3, tap coupling at point 16 is illustrated wherein a transmission line 18 is attached directly to the electrode. The tap spacing is adjusted to that of the transmission line impedance by techniques well known in the art. FIG. 7 illustrates an alternate method of coupling employing a coupling loop 28. This coupling method was used for the thermal measurements previously described. The impedance seen looking into the coupling loop 28 is a function of the spacing distance "S" and the loaded "Q" of the resonant cylinder. FIG. 8 illustrates the measured input impedance measured at 18 in FIG. 7 for various spacings "S". For example, in a tested embodiment, it was desired to feed the electrode with a 300 ohm line, thus, a spacing of 1.0 inches was employed. These measurements were made with the electrode loaded with an actual human hand inserted up to the wrist. The impedence varies from approximately 400 ohms when loaded with a small hand to approximately 190 ohms with a large arm inserted in the electrode.

Figure 9:
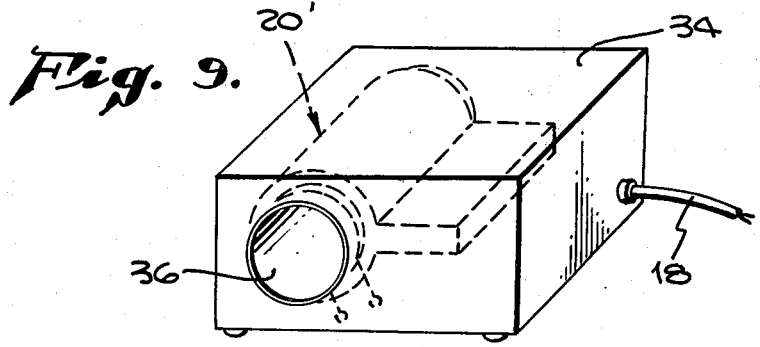
FIG. 9 is an electrode assembly according to the present invention suitably housed for patient use.

A convenient configuration for housing the electrode of the present invention for patient use is shown in FIG. 9. The electrode 20' is enclosed within a plastic box 34 having a plastic cylinder 36 therethrough into which the actual body portion is inserted. The metal cylinder of the electrode itself surrounds the plastic cylinder to prevent patient contact with the metal cylinder. The capacitor plates extend sideward into the housing area provided therefor. The transmission line is attached to an internal loop 28 so that the working assembly contained therein is of the configuration shown in FIG. 7 but with stacked electrode plates as shown in FIGS. 4 and 5.

Wherefore, it can be seen that the electrode of the present invention has truly achieved its objective of providing an electrode of small diameter-to-length ratio wherein it is also possible to control the energy distribution and, therefore, the heating pattern along the electrode cylinder length.

Having thus described my invention, I claim:
1. An electrode for use in the treatment of animal tissue by hyperthermia comprising:
   (a) electrically conductive material in the form of a longitudinally slotted cylinder including means for coupling to a supply of radio frequency energy; and,
   (b) capacitor plates electrically and physically attached radially outward to respective sides of the slot in parallel-spaced relationship with a dielectric material disposed therebetween and being sized and spaced to make the electrode self-resonant at said radio frequency.
2. The electrode of claim 1 wherein:
   said capacitor plates comprise a plurality of stacked plates having tabs along one edge with the tabs of alternate plates electrically connected together to form two groups of plates and with the tabs from the two groups attached to respective sides of the slot in said cylindrical electrical conductive material.

3. The electrode of claim 1 or claim 2 and additionally comprising:

an enclosure having a pair of opposed openings in the sidewalls thereof and a cylinder of insulating material communicating between said openings, said cylindrical electrically conductive material being disposed within said enclosure around said cylinder of insulating material and said capacitor plates being disposed within said enclosure whereby the electrically conductive portions of the electrode are contained within said enclosure and an insulated path into the opening of the electrode is provided into which the animal tissue can be placed.

4. The electrode of claim 1 or claim 2 wherein:

said capacitor plates are attached to the cylinder along the slot only at pre-selected points which will impart desired power dissipation characteristics to the electrode.

5. The electrode of claim 4 wherein:

said capacitor plates are attached only adjacent the ends of the slot to produce a substantially even power dissipation along the length of the electrode.

6. The electrode of claim 4 wherein:

said capacitor plates are attached only adjacent the middle of the slot to produce a peaked power dissipation along the length of the electrode with the maximum power dissipation in the middle of the electrode between the points of attachment.

7. The electrode of claim 1 wherein:

said capacitor plates are attached continuously along the length of the slot in the cylinder.

8. An electrode for use in the treatment of animal tissue by hyperthermia comprising:

(a) a sheet of electrically conductive material formed into a cylinder having a longitudinal slot therein;
(b) means operably disposed for coupling a supply of radio frequency energy to said cylinder; and,
(c) a plurality of rectangular plates of electrically conductive material stacked with dielectric material therebetween, said plates each having a pair of tabs extending from one edge, said tabs on alternate plates being electrically connected to alternate sides of said slot, said plates being disposed radially outward and being of an area, the spacing therebetween, and the dielectric material such as to make the electrode self-resonant at the radio frequency employed.

9. The electrode of claim 8 wherein:

said tabs on adjacent plates are longitudinally offset from one another and said tabs on alternate plates are longitudinally aligned whereby two groups of capacitor plates are formed with one group being attached at two points by way of two stacks of tabs and the other being attached at two different points by way of two stacks of tabs.

10. The electrode of claim 9 wherein:

said tabs are angled such that when attached to said cylindrical material said capacitor plates extend radially outward therefrom.

11. The electrode of claim 9 wherein:

said tabs are attached to the cylinder along the slot only at pre-selected points which will impart desired power dissipation characteristics to the electrode.

12. The electrode of claim 11 wherein:

said tabs are attached only adjacent the ends of the slot to produce a substantially even power dissipation along the length of the electrode.

13. The electrode of claim 11 wherein:

said tabs are attached only adjacent the middle of the slot to produce a peaked power dissipation along the length of the electrode with the maximum dissipation in the middle thereof.

* * * * *